US008076635B2

(12) United States Patent
Geromanos et al.

(10) Patent No.: US 8,076,635 B2
(45) Date of Patent: Dec. 13, 2011

(54) APPARATUS AND METHOD FOR PERFORMING MASS SPECTROSCOPY

(75) Inventors: Scott J. Geromanos, Middletown, NJ (US); Guo-Zhong Li, Westborough, MA (US); Jeffrey C. Silva, Beverly, MA (US); Marc V. Gorenstein, Needham, MA (US); Hans Vissers, Huizen (NL)

(73) Assignee: Waters Technologies Corporation, Milford, MA (US)

( * ) Notice: Subject to any disclaimer, the term of this patent is extended or adjusted under 35 U.S.C. 154(b) by 339 days.

(21) Appl. No.: 12/301,469

(22) PCT Filed: May 24, 2007

(86) PCT No.: PCT/US2007/069657
§ 371 (c)(1),
(2), (4) Date: Apr. 8, 2009

(87) PCT Pub. No.: WO2007/140251
PCT Pub. Date: Dec. 6, 2007

(65) Prior Publication Data
US 2009/0224148 A1    Sep. 10, 2009

Related U.S. Application Data

(60) Provisional application No. 60/808,815, filed on May 26, 2006.

(51) Int. Cl.
*H01J 49/00* (2006.01)
*H01J 49/40* (2006.01)

(52) U.S. Cl. ............. 250/281; 250/282; 702/22; 702/28

(58) Field of Classification Search .............. 250/281, 250/282; 702/22, 23, 27, 28; 95/82, 83, 95/84; 96/101, 102, 103, 104
See application file for complete search history.

(56) References Cited

U.S. PATENT DOCUMENTS

2005/0092910 A1* 5/2005 Geromanos et al. .......... 250/282
2006/0131222 A1* 6/2006 Norton ....................... 210/198.2
2006/0293863 A1* 12/2006 Ruemer et al. ................. 702/83

FOREIGN PATENT DOCUMENTS

| WO | 03/054549 | 7/2003 |
|----|-----------|--------|
| WO | 2005/114930 | 1/2005 |
| WO | 2005/113830 | 12/2005 |

OTHER PUBLICATIONS

Silva, et al.; Waunatitative Proteomic Analysis by Accurate Mass Retention Time Pairs., Analytical Chemistry, Apr. 1, 2005, vol. 77, pp. 2187-2200.
Jensen, Ole N. et al; Identification of the Components of Simple Protein Mixtures by High-Accuracy Peptide Mass Mapping and Database Searching; Anal. Chem. vol. 69, No. 23, Dec. 1, 1997.
PCT Written Opinion form PCT/ISA/237 for PCT/US07/69657, dated Aug. 4, 2008.
PCT International Search Report, PCT/ISA220 /210 for PCT/US07/69657, dated Aug. 4, 2010.

\* cited by examiner

*Primary Examiner* — Robert Kim
*Assistant Examiner* — Nicole Ippolito Rausch
(74) *Attorney, Agent, or Firm* — Jamie H. Rose (57) ABSTRACT

Embodiments of the present invention are directed to apparatus and methods for performing mass spectrometry. Data pair information is subjected to an ion audit process in which data pair information that relates to scored compounds is subtracted from the data pair information. The depleted information more readily reveals data pair information for compounds present with smaller signals.

30 Claims, 5 Drawing Sheets

APPARATUS AND METHOD FOR PERFORMING MASS SPECTROSCOPY

CROSS REFERENCE TO RELATED APPLICATIONS

This application is the national stage of International Application No. PCT/US2007/069657, filed May 24, 2007 and designating the United States, which claims benefit of and priority to U.S. Provisional Application Ser. No. 60/808,815, filed May 26, 2006, the entire contents of which is hereby incorporated by reference in its entirety.

FIELD OF THE INVENTION

This invention relates to apparatus and methods for performing mass spectroscopy and, in particular, identifying compounds in a mixture by mass and chromatographic retention times.

BACKGROUND OF THE INVENTION

Mass spectrometry is a technique for determining the mass of a compound. Mass spectrometers are instruments that produce a mass to charge signal that can be processed or interpreted to suggest a mass of a compound. Mass spectrometers place a charge on molecule and accelerate the molecule to a detector. The detector produces a signal relating to the mass of the molecule and the charge carried on the molecule. Mass spectrometry is used to identify proteins and other compounds of biological origination.

Chromatography is a technique for separating compounds held in solution. Compounds held in a solution will exhibit different affinity for a solid medium in contact with the solution. As a solution flows past or through an immobile medium, the compounds separate from each other.

As used herein, the term "retention time" refers to the time a compound takes to exit from a column or cartridge or other separation device containing a solid separation medium.

As used herein, the term "sample" refers to the material being analyzed. Samples of biological origin are often complex mixtures comprising proteins, precursors of such proteins, fragments of proteins and reaction products of proteins and other compounds. Proteins are capable of assuming different charge states and being fragmented. Often, the analysis of the sample may include an enzymatic digestion to cleave the sample at one or more known sites. These digestions may go to completion or leave incomplete digestion products. In a typical analysis, a sample comprising one or more proteins is placed in a vial and subjected to enzymatic digestion. The digested sample is passed to the chromatographic apparatus and separated into the products of the digestion.

It is common to combine chromatography with mass spectrometry. Chromatography is used to separate the compounds of a sample, which compounds are placed into a mass spectrometer. The mass spectrometer produces a mass to charge signal that can be related to a retention time.

The data produced in such a combination is complex and difficult to analyze. Methods and apparatus to analyze such chromatographic mass spectrometry data with greater specificity and fewer false identifications are desired.

SUMMARY OF THE INVENTION

Embodiments of the present invention are directed to methods and apparatus for analyzing samples. One embodiment of the present invention features an apparatus identifying compounds in a mixture by mass and chromatographic retention times. The apparatus comprises computer processing means placed in signal communication with a chromatographic apparatus and a mass spectrometer for receiving one or more signals from the chromatographic apparatus relating to retention time and one or more signals from a mass spectrometer relating to mass. The chromatographic apparatus and the mass spectrometer are in fluid communication to allow the chromatographic apparatus to receive samples and pass such samples to the mass spectrometer. The computer processing means correlates each mass signal to a retention time signal to form a data pair and data pair information for a plurality of data pairs, storing the data pair information, and sorting the data pair information into groups defined by a range of retention times into bins. The computer processing means has data base means comprising mass and retention time information for known compounds. The computer processing means initiating an ion audit process having a first pass.

The first pass of the ion audit process comprises the step of specifying matching criteria for data pair information present in a bin or a plurality of bins, potentially representing a compound, to form match parameters and identifying a group of data pairs corresponding to the match parameters, said data pairs corresponding to the match parameters forming a matched set. Next, the matched set is compared to the data base means and identifying a compound corresponding to at least one of the match parameters and assigning an identification to the data pairs of the matched set to form an scored compound. The data pairs of the matched set is subtracted from the bins to form one or more depleted bins. This process is repeated with the data pair information held in the one or more bins and depleted bins, until the ion audit process associates all data pair information with compounds, fragments of compounds and reaction products of compounds, or the match criteria for remaining compounds, fragments of compounds and reaction products of compounds do not correspond to information in the data base, or a user defined number of repetitions.

Preferably, the ion audit process focuses on the dominant signals, the audit clears such signals from the data pair information to allow identification of the next dominant signal group. Thus, as the audit progresses, the lower intensity signals are revealed with ever greater clarity.

The term "computer processing means" is used to denote software and firmware for use by computers, programmed computer processing units (CPUs), personal computers, servers, mainframe computers, computers and CPUs integrated with chromatographic apparatus or mass spectrometers or other analytical instrumentation.

The term "communication", with reference to fluids, means plumbed together. The term "communication" with reference to signals, means wired, or optically linked, or radio signal linked as in wireless communication so as to receive and/or emit signals.

The term "correlates" is used to denote linking or combining. For example, combining a retention time with a mass to charge signal means that the mass to charge signal which was produced by a ion with a defined retention time is held together a pair of values, a data pair. The term "bin" or "bins" is used to denote a group of such data pairs with common or similar features. The present application forms bins with a range of retention times. That is, the total time of a separation is divided into a plurality of time periods.

The term "data base means" refers to an archive of information. This data base means can be developed by a user from data developed and stored in one or more computers, a commercially available data base available through network systems, such as the internet, or available through access through storage devices and the like.

The term "matching criteria" refers to values that fall within a defined range. This matching criteria may be a cluster or grouping of values. The term "parameters" is used to denote the values that are used to compare values found in the data pairs or in the data base. Data pairs that comport with the parameters are grouped in matched sets.

A "scored compound" is the putative identity of the compound that is represented by the set of data pairs. The identity may have different degrees of confidence, which upon further analysis of the data may increase or decrease.

Preferably, the ion audit process comprises specifying matching criteria for data pair information present in a bin, depleted bin or a plurality of bins or depleted bins, potentially representing one or more fragments of the scored compound, to form fragment match parameters. Next, a group of data pairs corresponding to the fragment match parameters are identified to form a group of data pairs forming a fragment associated matched set. The fragment associated matched set is subtracted from the bins and depleted bins. The further depleted bins have fewer data pairs allowing other groups of data pairs to be recognized with greater clarity. The data pairs which represent fragments of the scored compound are used to increase confidence in the compound identification.

Preferably, the ion audit comprises specifying matching criteria for data pair information present in a bin or depleted bin or a plurality of bins or depleted bins, potentially representing one or more precursors of the scored compound, to form precursor match parameters. Next, a group of data pairs corresponding to the precursor match parameters are identified, to form a group of data pairs forming a precursor associated matched set. The precursor associated matched set is subtracted from the bins and depleted bins. The further depleted bins have fewer data pairs allowing other groups of data pairs to be recognized with greater clarity. The data pairs which represent precursors of the scored compound are used to increase confidence in the compound identification.

The term "precursor" is used to denote both an incomplete digestion product of a protein or a larger protein from which the scored protein is made or smaller parts of a protein which are condensed or folder together to form a protein. For example, in vivo, proteins are synthesized with added amino acids or peptide units that may function in establishing the tertiary structure, that is, how the protein folds onto itself, these added amino acids or peptide units may be lost or removed to produce the active protein.

Preferably, the ion audit comprises specifying matching criteria for data pair information present in a bin or depleted bin or a plurality of bins or depleted bins, potentially representing reaction products of the scored compound, to form reaction product match parameters. Next, data pairs which correspond to the reaction product match parameters are identified to form a group of data pairs forming a reaction product associated matched set. The reaction product associated matched set is subtracted from the bins and depleted bins. Again, the further depleted bins have fewer data pairs allowing other groups of data pairs to be recognized with greater clarity. The data pairs which represent reaction products of the scored compound are used to increase confidence in the compound identification.

The apparatus can perform the ion audit in a single pass of all bins or a subset or a single bin. However, it is preferable to apply the subtraction to a plurality of bins such that data pairs associated with a putative compound are removed and other details seen.

Preferably, the ion audit process includes a second pass, wherein for a scored compound, at least one selected from the group consisting of anticipated fragments, anticipated precursors and anticipated reaction products thereof, are identified from the data base for the scored compound. Matching criteria for data pair information present in one or more bins to form are specified defining second pass match parameters to said selected anticipated fragment, anticipated precursor and anticipated reaction product thereof. Data pairs which correspond to said second pass match parameters are identified to form a group of data pairs forming a second pass matched set. The second pass matched set is subtracted from said bins and depleted bins.

Again, the further depleted bins have fewer data pairs allowing other groups of data pairs to be recognized with greater clarity. The data pairs which represent anticipated fragments, anticipated precursors and anticipated reaction products of the scored compound are used to increase confidence in the compound identification.

The term "anticipated fragment" is used in the sense of incomplete digestions of a protein, or a fragment that is normally encountered in mass spectrometers having a fragmentation chamber. In the event the chromatographic apparatus receives a digest of a sample, incomplete digestion processes can be anticipated.

In the event the mass spectrometer has a fragmentation chamber, the compounds can be expected to form fragments. A preferred mass spectrometer has a fragmentation chamber and has a low energy mode in which fragments are not formed and a high energy mode in which fragments are made. A preferred mass spectrometer can switch from high to low energy mode within a time interval smaller than the interval associated with the bins.

The term "anticipated reaction product" is used to denote common methylated, oxidized phosphorylated and glycosylated derivatives of the compounds and the fragments, and precursors of the compounds. Anticipated precursors are molecules from which the compounds are made which would be expected to be present in a sample.

Preferably, the apparatus further comprises or is used with data output means for displaying the compounds identified in the ion audit process. The data output means may comprise printers, video output devices, such as video monitors, screen displays, projectors.

The apparatus further comprises or is used with chromatograph apparatus for receiving a sample and separating said sample into compounds by retention time. The chromatographic apparatus is in signal communication with computer processing means to produce a signal from which retention time can be determined.

The apparatus further comprises or is used with a mass spectrometer for receiving compounds from the chromatographic apparatus and producing a signal corresponding to the mass of the compound. And in the event said compound forms one or more fragments, a signal corresponding to a fragment, and in the event the compound reacts to form a reaction product, a signal corresponding to said reaction product, and in the event the compound is present as a precursor, a signal corresponding to the precursor, the mass spectrometer in signal communication with said computer processing means to produce a mass signal relating to the mass of a compound, fragment, reaction product or precursor;

A further embodiment of the present invention is directed to a method of identifying a compound with chromatographic apparatus and mass spectrometry apparatus. The chromatographic apparatus receives a sample and separates the sample into compounds by retention time. And, the chromatographic apparatus produce a signal from which retention time can be determined. The mass spectrometer receives one or more compounds from the chromatographic apparatus and produces a signal corresponding to the mass of the compound. And, in the event the compound forms one or more fragments, a signal corresponding to a fragment, and in the event the compound reacts to form a reaction product, a signal corresponding to the reaction product, and in the event the compound is present as a precursor, a signal corresponding to the precursor. The method comprising an ion audit process having the steps of correlating each mass signal to a retention time signal to form a data pair and data pair information for a plurality of data pairs, storing the data pair information, and sorting said data pair information into groups defined by a range of retention times into bins. The method further comprises the step of specifying matching criteria for data pair information present in a bin or a plurality of bins, potentially representing a compound, to form match parameters. And, the method comprises the step of identifying a group of data pairs corresponding to the match parameters, the data pairs corresponding to the match parameters forming a matched set. Next, the matched set are compared with data base means and a compound is identified that corresponds to at least one of the match parameters to assign an identification to the data pairs of the matched set to form an scored compound. The data pair information of said matched set are subtracted from the bins to form one or more depleted bins. The ion audit of the present invention repeats the steps of specifying matching criteria through the step of subtracting data pair information from the bins and depleted, until all data pair information is associated with compounds, fragments of compounds and reaction products of compounds, or the match criteria for remaining compounds, fragments of compounds and reaction products of compounds do not correspond to information in the data base, or a user defined number of repetitions.

Preferably, the method comprises the step of specifying matching criteria for data pair information present in a bin or a plurality of bins, potentially representing one or more fragments of the scored compound, to form fragment match parameters. Next, a group of data pairs corresponding to the fragment match parameters are identified to form a group of data pairs forming a fragment associated matched set. The data pair information of fragmented associated matched sets is subtracted from the bins and depleted bins. The data pairs which represent fragments of the scored compound are used to increase confidence in the compound identification. Removal of the data pair information allows other features of the data to be seen.

Preferably, the method comprises the step of specifying matching criteria for data pair information present in a bin or a plurality of bins, potentially representing one or more precursors of the scored compound, to form precursor match parameters. Next, a group of data pairs corresponding to said precursor match parameters are identified to form a group of data pairs forming a precursor associated matched set. The data pair information of the precursor associated matched set is subtracted from the bins and depleted bins. The data pairs which represent precursors of the scored compound are used to increase confidence in the compound identification. Removal of the data pair information allows other features of the data to be seen.

Preferably, the method comprises the steps of specifying matching criteria for data pair information present in a bin or a plurality of bins, potentially representing a reaction products of the scored compound, to form reaction product match parameters. Data pairs which correspond to said reaction product match parameters are identified to form a group of data pairs forming a reaction product associated matched set. The data pair information of the reaction product associated matched set is subtracted from the bins and depleted bins. The data pairs which represent reaction products of the scored compound are used to increase confidence in the compound identification. Removal of the data pair information allows other features of the data to be seen.

The method of the present invention can be performed in a single first pass or in multiple passes. Preferably, the ion audit process includes a second pass, wherein for a scored compound at least one selected from the group consisting of anticipated fragments, anticipated precursors and anticipated reaction products thereof is chosen for a second pass. The second pass follows a first pass or a first series of passes in which the specifying criteria remains substantially unchanged.

These and other features and advantages of the present invention will be apparent to those skilled in the art from viewing the Figures and reading the detailed description that follows.

DETAILED DESCRIPTION OF THE INVENTION

The present invention will now be described with reference to the Figures with respect to methods and apparatus for analyzing samples. The descriptions in this regard will highlight the use of the invention for chemical analysis of proteins and peptides. However, those skilled in the art will recognize that embodiments of the present invention have broader application for the analysis of other compounds or compositions, polymers, and biopolymers including without limitation, nucleic acids, carbohydrates, and synthetic polymers.

Figure 1:
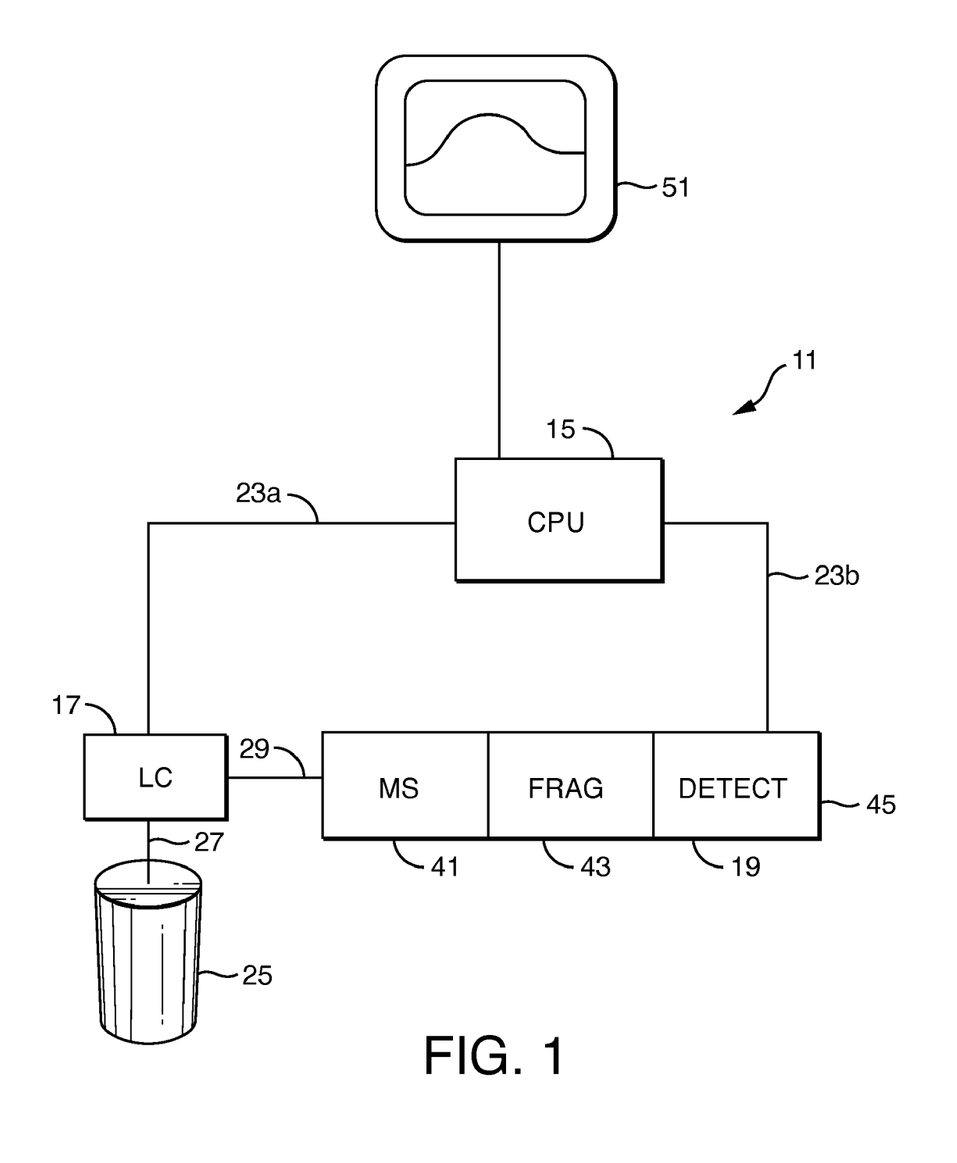
FIG. 1 is a diagram of an apparatus embodying features of the present invention.

An apparatus embodying features of the present invention, generally designated by the numeral 11, is depicted in FIG. 1. The apparatus is used to identify compounds in a mixture by mass and chromatographic retention times. The apparatus comprises the following major elements; computer processing means 15, a chromatographic apparatus 17, and a mass spectrometer 19.

As depicted, the computer processing means 15 suggests a computer or CPU. However, the computer processing means 15 may comprise software or firmware, loaded on a computer, CPU or server mainframe computer or CPU integrated with other analytical equipment, including by way of example, the chromatographic apparatus 17 and mass spectrometer 19. Software is commonly programmed to the memory of a computer by means of a computer readable device or disk or networks having access to the computer program. Once programmed, the software is considered firmware. Computers and CPUs are known in the art and sold by numerous vendors. IBM format computers are sold by Dell Computer Corporation and others. Apple format computers are sold by Apple Corporation (California, USA). By way of example, computer processing means 15 may comprise s computer programs integrated into larger software programs for managing the operation of analytical instruments, data management and data processing. Such larger software programs are sold by several vendors under the trademarks MILLENNIUM®, EMPOWER™ (Waters Corporation, Milford, Mass., USA), CHEMSTATION™ (Agilent Corporation, Palo Alto, Calif., USA), MASSLINKS® (Micromass UK Ltd, Manchester, England) and others.

Computer processing means 15 is in signal communication with chromatographic apparatus 17 and a mass spectrometer 19 as depicted by lines 23a and 23b. Those skilled in the art will recognize that the line 23a and line 23b can be replaced with wireless communication devices and routers. Line 23a and line 23b can be wires for electrical magnetic signals or represent optical communication means such as fiber optic cable.

Computer processing means 15 is in signal communication with chromatographic apparatus 17 and mass spectrometer 19. Chromatographic apparatus 17 comprises any number of chromatographic apparatus including by way of example without limitation, liquid and gas chromatographic instruments. Chromatographic apparatus typically have a pump for propelling a fluid [not shown] and conduits for carrying the fluid. Chromatographic instruments receive sample from a sample manager or sample injection device [not shown]. As depicted, the chromatographic apparatus 17 is in fluid communication with a sample held in a vial 25 by means of a conduit 27. This sample, when proteins and peptides are anticipated, held in vial 25, is subjected to digestion means such as enzymes and the like. This causes the proteins and peptides to form one or more digestion products.

Chromatographic instruments receive and place a sample into a solvent flowing in a conduit [not shown]. The solvent is received in a separation device [not shown] such as a capillary, column or cartridge. Columns and cartridges are commonly packed or contain a separation media which interacts with the sample compounds in the solvent. These compounds will exhibit different affinity for the separation media and will be retained and separate. The period of time the compounds are retained is known as the retention time.

Chromatographic apparatus 17 produces one or more signals which are communicated to the computer processing means relating to retention time. Chromatographic apparatus of the type depicted are available from several vendors under the tradenames ALLIANCE® and ACQUITY® from Waters Corporation and 1100™ from Agilent GmbH of (Germany).

As depicted, chromatographic apparatus 17 is in fluid communication with mass spectrometer 19 by means of a conduit 29. However, fluid communication, in this sense, does not require that the mass spectrometer 19 receives sample from the chromatographic apparatus 17 by means of a conduit 29. The mass spectrometer 19 may receive sample related to retention time by deposition on a solid surface in the nature of MALDI or DIOS process.

The mass spectrometer 19 produces a signal relating to mass, and, more precisely relating to the mass to charge ratio of a compound. Mass spectrometer 19 is illustrated as a triple quadrupole mass spectrometer having a first mass selection chamber 31, a fragmentation chamber 33 and a mass detection chamber 35. The first mass detection chamber 31 selects an ion or group of ions by mass to charge ratio. The ions may be allowed to pass through the fragmentation chamber 35 or subjected to energy which causes the ions to from fragments. The ions and ion fragments are passed to the mass detection chamber 35.

Mass spectrometers such as mass spectrometer 19 are available from several vendors including Waters Corporation (Milford, Mass., USA), Thermo Finnigan (Waltham, Mass., USA), Agilent Corporation (Palo Alto, Calif., USA) and others.

The computer processing means 15 correlates each mass signal to a retention time signal to form a data pair or group. By way of example, the data may be organized as set forth in Table 1 below:

TABLE 1

| MH+ | Intensity | Retention time | Charge State |
|---|---|---|---|
| 484.7397 | 110 | 43.556 | 1 |

The data pair information for a plurality of data pairs is stored. The data pair information may comprise a thousand fold lines of the type set forth above, or gigabytes of information. This large amount of information is difficult to interpret. To aid in the interpretation of the data, the data is commonly plotted and graphs and examined for peaks and patterns representing ions and ion fragments.

In accordance with the present invention, the data pair information is sorted, by the computer processing means 15, into groups defined by a range of retention times into bins. The computer processing means 15 has data base means comprising mass and retention time information for known compounds. The computer processing means 15 initiates an ion audit process having at least one first pass which is described below. The data base of the computer processing means 15 may comprise stored data in the computer or data held in a data storage system or network.

The first pass of the ion audit process comprises the step of specifying matching criteria for data pair information present in a bin or a plurality of bins, potentially representing a compound, to form match parameters. That is, the data pair information is examined for data pairs having the highest intensity representing a compound which compound is present in substantial quantity.

The computer processing means 15 identifies a group of data pairs corresponding to the match parameters forming a matched set. Next, the computer processing means compares the matched set to the data base means and identifying a compound corresponding to at least one of the match parameters. The computer processing means 15 assigns an identification to the data pairs of the matched set to form a scored compound. The computer processing means 15 subtracts the data pairs of the matched set from the bins to form one or more depleted bins.

This process is repeated with the data pair information held in the one or more bins and depleted bins, until the ion audit process associates all data pair information with compounds, fragments of compounds and reaction products of compounds, or the match criteria for remaining compounds, fragments of compounds and reaction products of compounds do not correspond to information in the data base, or a user defined number of repetitions.

Preferably, the ion audit process focuses on the dominant signals; the audit clears such signals from the data pair information to allow identification of the next dominant signal group. Thus, as the audit progresses, the lower intensity signals are revealed with ever greater clarity.

Figure 2A:
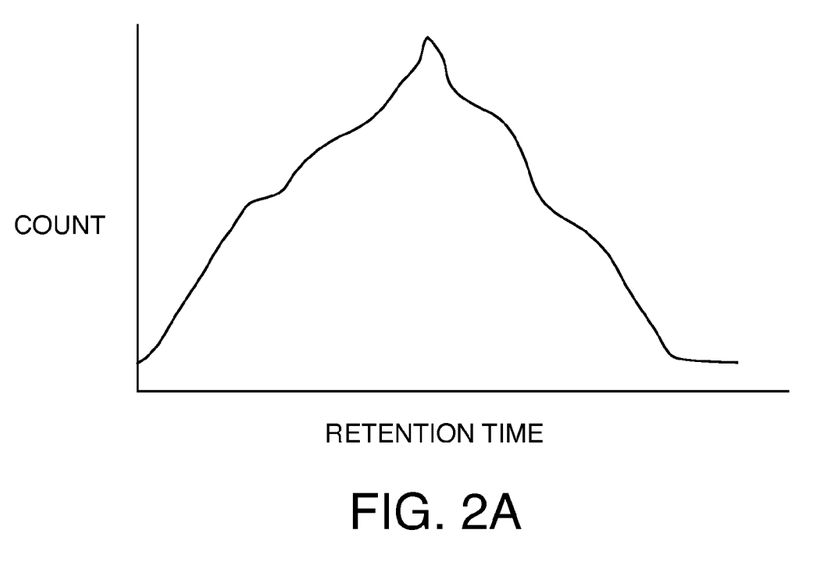
FIG. 2a is a spectrum of binned data pairs without depleting the bins.
Figure 2B:
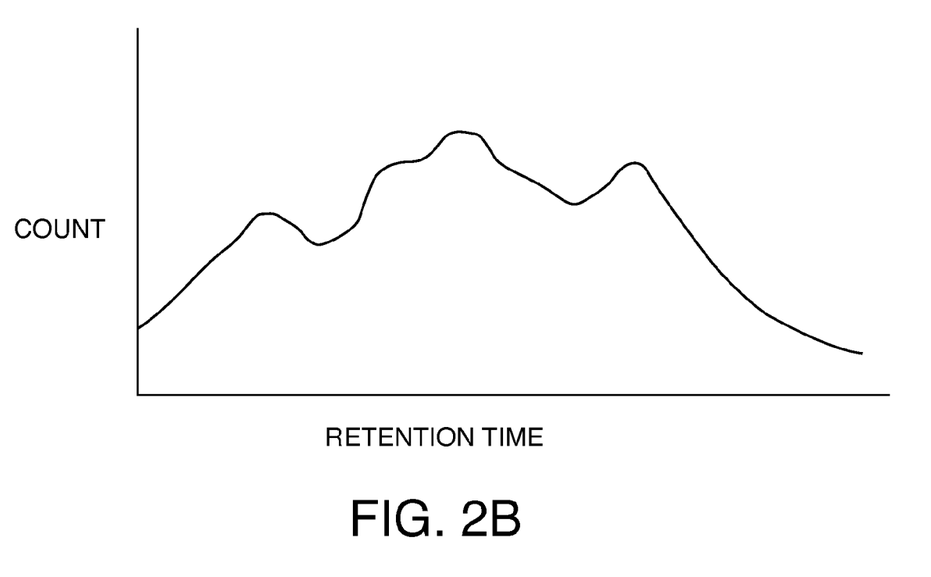
FIG. 2b is a spectrum of depleted binned data pairs.

FIG. 2a graphically depicts the binned data pairs by count and retention time. Only a single peak is observed. However, upon subtracting the information of the data pairs for which a scored compound has been made, three smaller peaks become apparent. These smaller peaks may comprise additional compounds.

Preferably, the ion audit process comprises specifying matching criteria for data pair information present in a bin, depleted bin or a plurality of bins or depleted bins, potentially representing one or more fragments of the scored compound, to form fragment match parameters. Next, a group of data pairs corresponding to the fragment match parameters are identified to form a group of data pairs forming a fragment associated matched set. The fragment associated matched set is subtracted from the bins and depleted bins. The further depleted bins have fewer data pairs allowing other groups of data pairs to be recognized with greater clarity. The data pairs which represent fragments of the scored compound are used to increase confidence in the compound identification.

Preferably, the ion audit comprises specifying matching criteria for data pair information present in a bin or depleted bin or a plurality of bins or depleted bins, potentially representing one or more precursors of the scored compound, to form precursor match parameters. Next, a group of data pairs corresponding to the precursor match parameters are identified, to form a group of data pairs forming a precursor associated matched set. The precursor associated matched set is subtracted from the bins and depleted bins. The further depleted bins have fewer data pairs allowing other groups of data pairs to be recognized with greater clarity. The data pairs which represent precursors of the scored compound are used to increase confidence in the compound identification.

Preferably, the ion audit comprises specifying matching criteria for data pair information present in a bin or depleted bin or a plurality of bins or depleted bins, potentially representing reaction products of the scored compound, to form reaction product match parameters. Next, data pairs which correspond to the reaction product match parameters are identified to form a group of data pairs forming a reaction product associated matched set. The reaction product associated matched set is subtracted from the bins and depleted bins. Again, the further depleted bins have fewer data pairs allowing other groups of data pairs to be recognized with greater clarity. The data pairs which represent reaction products of the scored compound are used to increase confidence in the compound identification.

The apparatus can perform the ion audit in a single pass of all bins or a subset or a single bin. However, it is preferable to apply the subtraction to a plurality of bins such that data pairs associated with a putative compound are removed and other details seen.

Preferably, the ion audit process includes a second pass, wherein for a scored compound, at least one selected from the group consisting of anticipated fragments, anticipated precursors and anticipated reaction products thereof, are identified from the data base for the scored compound. Matching criteria for data pair information present in one or more bins to form are specified defining second pass match parameters to said selected anticipated fragment, anticipated precursor and anticipated reaction product thereof. Data pairs which correspond to said second pass match parameters are identified to form a group of data pairs forming a second pass matched set. The second pass matched set is subtracted from said bins and depleted bins. A preferred second pass is directed to the anticipated reaction products.

Thus, applying the process to all bins for a scored compound allows the data pair information to be simplified, reduces the dominance of the larger signals to allow lesser signals to be seen and identified. These lesser signals may be obscured in bins not the initial focus of the scored compound but are revealed as signals associated with precursors, fragments and reaction products are removed.

Mass spectrometer 19 has a first mass selection chamber 41, fragmentation chamber 43 and a second mass detection chamber 45. The first mass selection chamber 41 selects ions of a selected mass charge ratio and passes such ions to the fragmentation chamber 43. The fragmentation chamber 43 can operate at low energy levels and high energy levels. At low energy levels the compounds entering the fragmentation chamber 43 are not broken into fragments and are passed to the second mass detection chamber 45 where such ions create a signal sent to the computer processing means 15. At high energy levels, the fragmentation chamber 43 causes the ions to form one or more fragments of the original compound. The fragments are passed to the second mass detection chamber 45 where such ions create a signal sent to the control means.

Mass spectrometer 19 can switch from high to low energy mode under the control of the computer processing means 15. Computer processing means 15 preferably sets a time interval for cycling between the high and low energy levels smaller than the interval associated with the bins. Thus, mass spectrometers 19 with fragmentation chambers 43 are used advantageously with the computer processing means 15 to cycle between high and low energy such that fragments can be more readily be associated with the parent compounds.

The apparatus 11 further comprises or is used with data output means 51 in the form of a monitor for displaying the compounds identified in the ion audit process. Those skilled in the art will recognize that the data output means may comprise, in addition or in place of the monitor, printers, other video output devices, such as televisions, cathode ray tubes, LCD screen, projectors and the like.

An embodiment of the present invention, directed to a method of identifying a compound, will be described with respect to the apparatus 11. The chromatographic apparatus 17 receives a sample and separates the sample into compounds by retention time. The chromatographic apparatus 17 produces a signal from which retention time can be determined. The mass spectrometer 19 receives one or more compounds from the chromatographic apparatus 17 and produces a signal corresponding to the mass of the compound. And, in the event the compound forms one or more fragments, a signal corresponding to a fragment, and in the event the compound reacts to form a reaction product, a signal corresponding to the reaction product, and in the event the compound is present as a precursor, a signal corresponding to the precursor.

Figure 3:
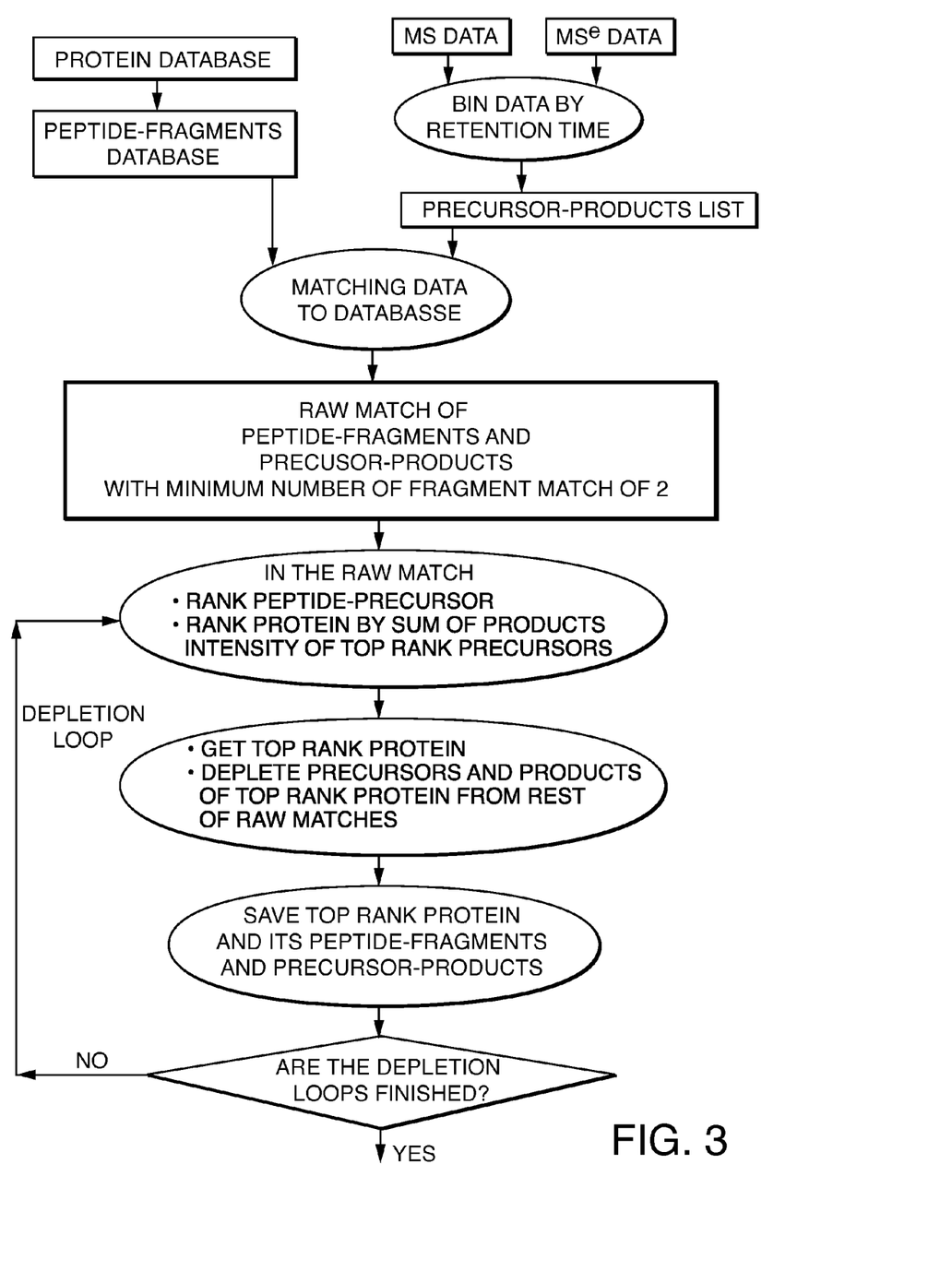
FIG. 3 is a flow diagram of an apparatus and method embodying features of the present invention.

Turning now to FIG. 3, which depicts a flow diagram of the method, the method comprising an ion audit process having the steps of correlating each mass signal to a retention time signal to form a data pair and data pair information for a plurality of data pairs, storing the data pair information, and sorting the data pair information into groups defined by a range of retention times into bins. The method further comprises the step of specifying matching criteria for data pair information present in a bin or a plurality of bins, potentially representing a compound, to form match parameters. And, the method comprises the step of identifying a group of data pairs corresponding to the match parameters, the data pairs corresponding to the match parameters forming a matched set. Next, the matched set are compared with data base means and a compound is identified that corresponds to at least one of said match parameters to assign an identification to the data pairs of the matched set to form an scored compound. The data pair information of said matched set are subtracted from said bins to form one or more depleted bins. The ion audit of the present invention repeats the steps of specifying matching criteria through the step of subtracting data pair information from the bins and depleted, until all data pair information is associated with compounds, fragments of compounds and reaction products of compounds, or the match criteria for remaining compounds, fragments of compounds and reaction products of compounds do not correspond to information in the data base, or a user defined number of repetitions.

Figure 4A:
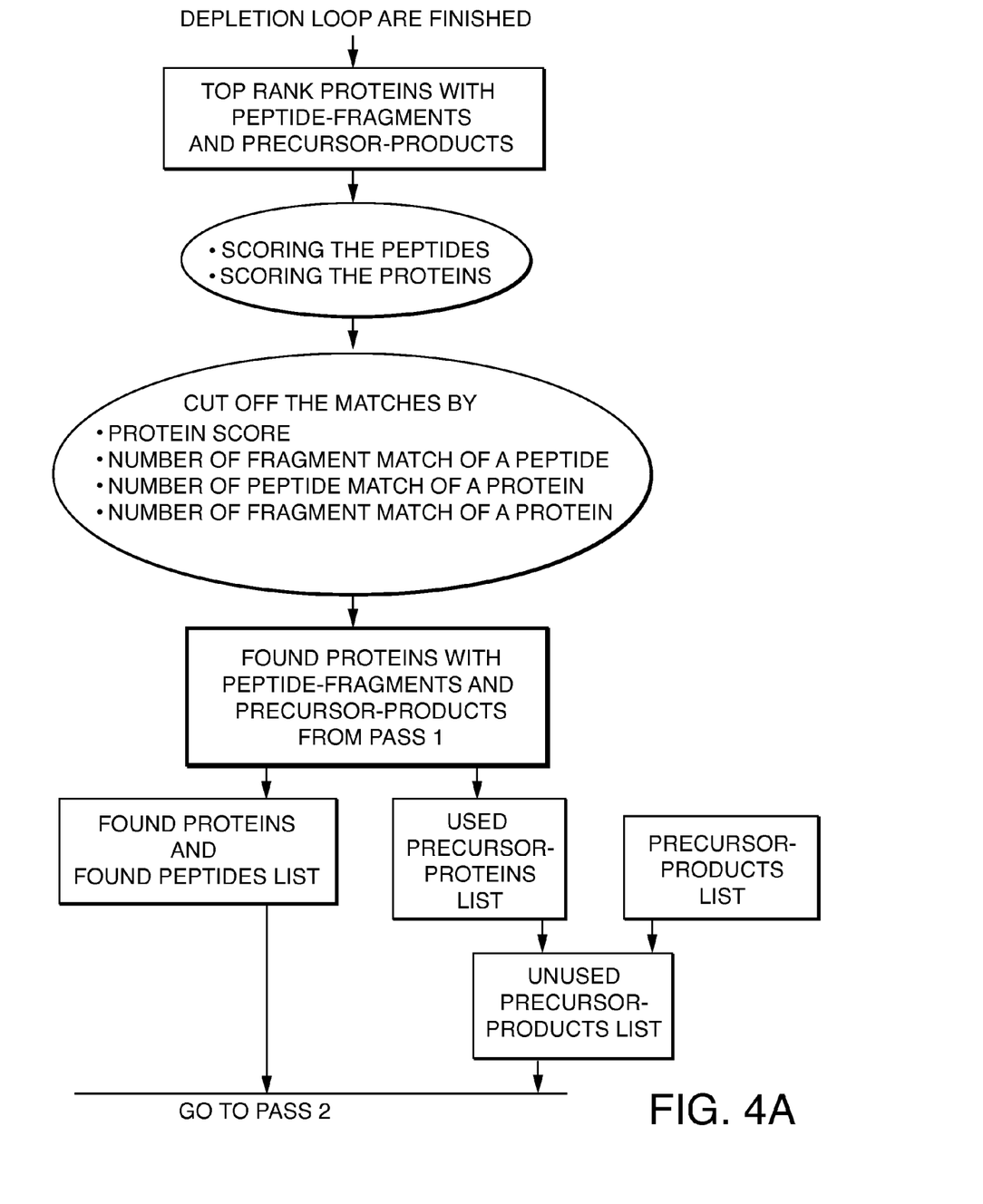
FIGS. 4a and 4b are a flow diagram of an apparatus and method embodying features of the present invention.
Figure 4B:
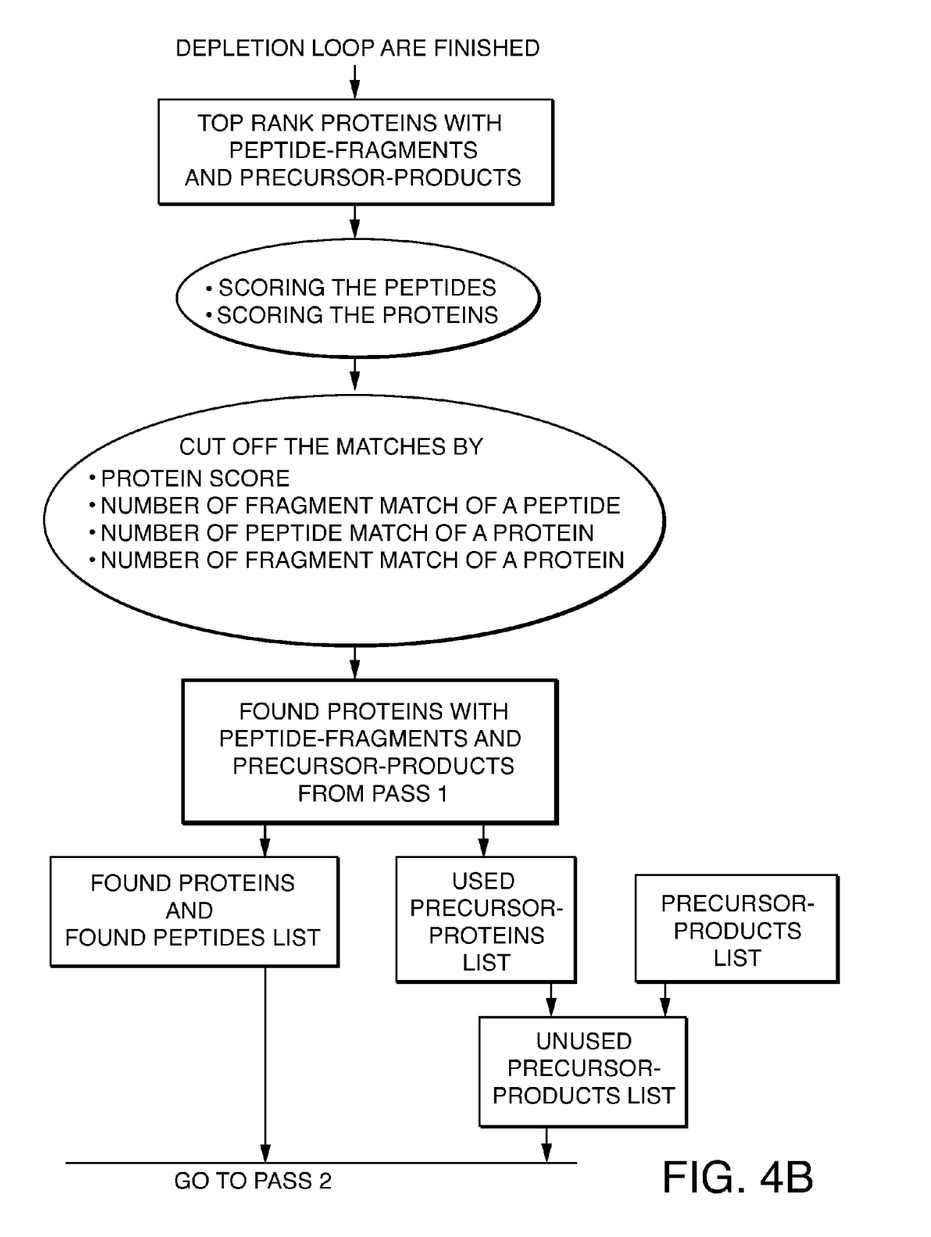

Preferably, the method comprises the step of specifying matching criteria for data pair information present in a bin or a plurality of bins, potentially representing one or more fragments of the scored compound, to form fragment match parameters. Next, a group of data pairs corresponding to the fragment match parameters are identified to form a group of data pairs forming a fragment associated matched set. The data pair information of fragmented associated matched sets is subtracted from the bins and depleted bins. The data pairs which represent fragments of the scored compound are used to increase confidence in the compound identification. Removal of the data pair information allows other features of the data to be seen. This is further illustrated as a continuous process in FIG. 4.

Preferably, the method comprises the step of specifying matching criteria for data pair information present in a bin or a plurality of bins, potentially representing one or more precursors of the scored compound, to form precursor match parameters. Next, a group of data pairs corresponding to said precursor match parameters are identified to form a group of data pairs forming a precursor associated matched set. The data pair information of the precursor associated matched set is subtracted from the bins and depleted bins. The data pairs which represent precursors of the scored compound are used to increase confidence in the compound identification. Removal of the data pair information allows other features of the data to be seen.

Preferably, the method comprises the steps of specifying matching criteria for data pair information present in a bin or a plurality of bins, potentially representing a reaction products of the scored compound, to form reaction product match parameters. Data pairs which correspond to said reaction product match parameters are identified to form a group of data pairs forming a reaction product associated matched set. The data pair information of the reaction product associated matched set is subtracted from the bins and depleted bins. The data pairs which represent reaction products of the scored compound are used to increase confidence in the compound identification. Removal of the data pair information allows other features of the data to be seen.

The method of the present invention can be performed in a single first pass or in multiple passes. FIGS. 4a and 4b depict a continuous process performed in a plurality of passes. Preferably, the ion audit process includes a second pass, wherein for a scored compound at least one selected from the group consisting of anticipated fragments, anticipated precursors and anticipated reaction products thereof is chosen for a second pass. The second pass follows a first pass or a first series of passes in which the specifying criteria remains substantially unchanged.

Returning now to FIG. 1, preferred method is performed by computer processing means 15 by means of software. An outline of the software program is set forth in the following sixteen pages. Software programmers are able to readily develop source code directed to the invention described herein and in reference to the outline.

Thus, the present invention has been described with respect to preferred embodiments with the understanding that those skilled in the art will be able to make alterations and modifications to the invention. Therefore, the invention should not be limited to the precise details set forth herein but should encompass the subject matter of the following claims and their equivalents.

The invention claimed is:

1. An apparatus for identifying compounds in a mixture by mass and chromatographic retention times comprising:
   computer processing means for being placed in signal communication with a chromatographic apparatus and a mass spectrometer, for receiving a signal from said chromatographic apparatus relating to retention time and said mass signal from said mass spectrometer, said computer processing means correlating each mass signal to a retention time signal to form a data pair and data pair information for a plurality of data pairs, storing the data pair information, and sorting said data pair information into groups defined by a range of retention times into bins, said computer processing means having data base means comprising mass and retention time information for known compounds, said computer processing means initiating an ion audit process having a first pass comprising:
   1) specifying matching criteria for data pair information present in a bin or a plurality of bins, potentially representing a compound, to form match parameters and identifying a group of data pairs corresponding to said match parameters, said data pairs corresponding to said match parameters forming a matched set;
   2) comparing said matched set with said data base means and identifying a compound corresponding to at least one of said match parameters and assigning an identification to said data pairs of said matched set to form a scored compound, and subtracting said data pairs of said matched set from said bins to form one or more depleted bins; and
   3) repeating steps 1 and 2 with the data pair information held in said one or more bins and depleted bins, until said ion audit process associates all data pair information with compounds, fragments of compounds and reaction products of compounds, or said match criteria for remaining compounds, fragments of compounds and reaction products of compounds do not correspond to information in said data base, or a user defined number of repetitions.

2. The apparatus of claim 1 wherein said ion audit comprises specifying matching criteria for data pair information present in a bin or a plurality of bins, potentially representing one or more fragments of said scored compound, to form fragment match parameters and identifying a group of data pairs corresponding to said fragment match parameters to form a group of data pairs forming a fragment associated matched set, and subtracting said fragmented associated matched set from said bins and depleted bins.

3. The apparatus of claim 2 wherein said data pairs which represent fragments of said scored compound are used to increase confidence in the compound identification.

4. The apparatus of claim 1 wherein said ion audit comprises specifying matching criteria for data pair information present in a bin or a plurality of bins, potentially representing one or more precursors of said scored compound, to form precursor match parameters and identifying a group of data pairs corresponding to said precursor match parameters, to form a group of data pairs forming a precursor associated matched set, and subtracting said precursor associated matched set from said bins and depleted bins.

5. The apparatus of claim 4 wherein said data pairs which represent precursors of said scored compound are used to increase confidence in the compound identification.

6. The apparatus of claim 1 wherein said ion audit comprises specifying matching criteria for data pair information present in a bin or a plurality of bins, potentially representing a reaction products of said scored compound, to form reaction product match parameters and identifying data pairs which correspond to said reaction product match parameters to form a group of data pairs forming a reaction product associated matched set, and subtracting said reaction product associated matched set from said bins and depleted bins.

7. The apparatus of claim 1 wherein said ion audit process includes a second pass, wherein for a scored compound at least one selected from the group consisting of anticipated fragments, anticipated precursors and anticipated reaction products thereof are identified from the data base for said scored compound and specifying matching criteria for data pair information present in one or more bins to form second pass match parameters to said selected anticipated fragment, anticipated precursor and anticipated reaction product thereof, identifying data pairs which correspond to said second pass match parameters to form a group of data pairs forming a second pass matched set, and subtracting said second pass matched set from said bins and depleted bins.

8. The apparatus of claim 7 wherein said data pairs which represent anticipated fragments, anticipated precursors and anticipated reaction products of said scored compound are used to increase confidence in the compound identification.

9. The apparatus of claim 1 wherein said mass spectrometer has a fragmentation chamber and has a low energy mode in which fragments are not formed and a high energy mode in which fragments are made.

10. The apparatus of claim 9 wherein said mass spectrometer can switch from high to low energy mode within a time interval smaller than the interval associated with said bins.

11. The apparatus of claim 1 wherein said compounds are proteins and peptides.

12. The apparatus of claim 1 further comprising chromatograph apparatus for receiving a sample and separating said sample into compounds by retention time, said chromatographic apparatus in signal communication with computer processing means to produce a signal from which retention time can be determined.

13. The apparatus of claim 1 further comprising a mass spectrometer for receiving compounds from said chromatographic apparatus and producing a signal corresponding to the mass of the compound, and in the event said compound forms one or more fragments, a signal corresponding to a fragment, and in the event said compound reacts to form a reaction product, a signal corresponding to said reaction product, and in the event said compound is present as a precursor, a signal corresponding to said precursor, said mass spectrometer in signal communication with said computer processing means to produce a mass signal relating to the mass of a compound, fragment, reaction product or precursor.

14. A method of identifying a compound with chromatographic apparatus and mass spectrometry apparatus wherein chromatograph apparatus receives a sample and separates said sample into compounds by retention time, said chromatographic means producing a signal from which retention time can be determined, said mass spectrometer receives one or more compounds from said chromatographic apparatus and produces a signal corresponding to the mass of the compound, and in the event said compound forms one or more fragments, a signal corresponding to a fragment, and in the event said compound reacts to form a reaction product, a signal corresponding to said reaction product, and in the event said compound is present as a precursor, a signal corresponding to said precursor, said method comprising an ion audit process having the steps of:

a) correlating each mass signal to a retention time signal to form a data pair and data pair information for a plurality of data pairs, storing the data pair information, and sorting said data pair information into groups defined by a range of retention times into bins;

b) specifying matching criteria for data pair information present in a bin or a plurality of bins, potentially representing a compound, to form match parameters and identifying a group of data pairs corresponding to said match parameters, said data pairs corresponding to said match parameters forming a matched set;

c) comparing said matched set and associated matched sets with data base means and identifying a compound corresponding to at least one of said match parameters and assigning an identification to said data pairs of said matched set to form a scored compound, and subtracting said data pairs of said matched set from said bins to form one or more depleted bins; and     d) repeating steps b through c with the data pair information held in said one or more bins and depleted bins, until all data pair information is associated with compounds, fragments of compounds and reaction products of compounds, or said match criteria for remaining compounds, fragments of compounds and reaction products of compounds do not correspond to information in said data base, or a user defined number of repetitions.

15. The method of claim 14 wherein said ion audit comprises specifying matching criteria for data pair information present in a bin or a plurality of bins, potentially representing one or more fragments of said scored compound, to form fragment match parameters and identifying a group of data pairs corresponding to said fragment match parameters to form a group of data pairs forming a fragment associated matched set, and subtracting said fragmented associated matched set from said bins and depleted bins.

16. The method of claim 15 wherein said data pairs which represent fragments of said scored compound are used to increase confidence in the compound identification.

17. The method of claim 14 wherein said ion audit comprises specifying matching criteria for data pair information present in a bin or a plurality of bins, potentially representing one or more precursors of said scored compound, to form precursor match parameters and identifying a group of data pairs corresponding to said precursor match parameters, to form a group of data pairs forming a precursor associated matched set, and subtracting said precursor associated matched set from said bins and depleted bins.

18. The method of claim 17 wherein said data pairs which represent precursors of said scored compound are used to increase confidence in the compound identification.

19. The method of claim 14 wherein said ion audit comprises specifying matching criteria for data pair information present in a bin or a plurality of bins, potentially representing a reaction products of said scored compound, to form reaction product match parameters and identifying data pairs which correspond to said reaction product match parameters to form a group of data pairs forming a reaction product associated matched set, and subtracting said reaction product associated matched set from said bins and depleted bins.

20. The method of claim 19 wherein said data pairs which represent precursors of said scored compound are used to increase confidence in the compound identification.

21. The method of claim 14 wherein said ion audit process includes a second pass, wherein for a scored compound at least one selected from the group consisting of anticipated fragments, anticipated precursors and anticipated reaction products thereof are identified from the data base for said scored compound and specifying matching criteria for data pair information present in one or more bins to form second pass match parameters to said selected anticipated fragment, anticipated precursor and anticipated reaction product thereof, identifying data pairs which correspond to said second pass match parameters to form a group of data pairs forming a second pass matched set, and subtracting said second pass matched set from said bins and depleted bins.

22. The method of claim 21 wherein said data pairs which represent anticipated fragments, anticipated precursors and anticipated reaction products of said scored compound are used to increase confidence in the compound identification.

23. The method of claim 21 wherein said anticipated fragments comprise of incomplete digestions.

24. The method of claim 21 wherein said anticipated reaction products comprise at least one of the groups consisting of oxidized, methylated, phosphorylated and glycosylated fragments and precursors.

25. The method of claim 14 wherein said chromatographic means receives a digest of a sample.

26. The method of claim 14 wherein said mass spectrometer has a fragmentation chamber and has a low energy mode in which fragments are not formed and a high energy mode in which fragments are made and said method comprises the step of switching between said high and low energy modes.

27. The method of claim 26 wherein said mass spectrometer can switch from high to low energy mode within a time interval smaller than the interval associated with said bins and said method comprises switching between said high and low energy modes within said time interval smaller than said bin.

28. The method of claim 14 wherein said compounds are proteins and peptides.

29. The method of claim 14 wherein said matching criteria is directed to data pairs which represent the largest signal.

30. The method of claim 14 wherein said score reflects the confidence of the identification.

* * * * *